(12) United States Patent
Matsuda et al.

(10) Patent No.: US 8,420,697 B2
(45) Date of Patent: *Apr. 16, 2013

(54) TREATMENT OF ACUTE EXACERBATION OF ASTHMA AND REDUCTION OF LIKELIHOOD OF HOSPITALIZATION OF PATIENTS SUFFERING THEREFROM

(75) Inventors: Kazuko Matsuda, Beverly Hills, CA (US); Yuichi Iwaki, Palos Verdes Estates, CA (US); Kirk W. Johnson, Moraga, CA (US)

(73) Assignee: MediciNova, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,181

(22) Filed: Jun. 15, 2012

(65) Prior Publication Data

US 2012/0251632 A1    Oct. 4, 2012

Related U.S. Application Data

(63) Continuation of application No. 12/948,545, filed on Nov. 17, 2010.

(60) Provisional application No. 61/262,352, filed on Nov. 18, 2009, provisional application No. 61/392,917, filed on Oct. 13, 2010.

(51) Int. Cl.
*A01N 37/00* (2006.01)
*A61K 31/21* (2006.01)

(52) U.S. Cl.
USPC .......................................... 514/510; 514/506

(58) Field of Classification Search ........................ None
See application file for complete search history.

(56) References Cited

U.S. PATENT DOCUMENTS 6,133,266 A * 10/2000 Kitazawa et al. .......... 514/237.5
6,136,852 A    10/2000 Kitazawa et al.
2008/0081825 A1  4/2008 Nakai et al.

OTHER PUBLICATIONS

National Asthma Education and Prevention Program, Expert Panel Report 3: Guidelines for the Diagnosis and Management of Asthma (2007).*
Appel et al., "Epinephrine improves expiratory flow rates in patients with asthma who do not respond to inhaled metaproterenol sulfate," J Allergy Clin Immunol, 1989, 84(1):90-98.
Bogie et al., "Comparison of Intravenous Terbutaline Versus Normal Saline in Pediatric Patients on Continuous High-Dose Nebulized Albuterol for Status Asthmaticus," Pediatric Emergency Care, 2007, 23(6):355-361.
Browne et al., "Randomised trial of intravenous salbutamol in early management of acute severe asthma in children," Lancet, 1997, 349(9048):301-305.
Browne et al., "Single-dose intravenous salbutamol bolus for managing children with acute severe asthma in the emergency department:Reanalysis of data," Pediatr Crit Care Med, 2002, 3(2):117-123.
Dougherty RH et al: "Acute Exacerbations of Asthma: Epidemiology, Biology and the Exacerbation-Prone Phenotype", Author Manuscript—published in final edited form as: Clinical & Experimental Allergy, vol. 39, No. 2, pp. 193-202, Feb. 2009.
International Search Report and Written Opinion mailed Jan. 26, 2011 in International Appln No. PCT/US2010/57028.
Lazarus, "Emergency Treatment of Asthma," N Engl J Med, 2010, 363:755-764.
National Asthma Education and Prevention Program, "Expert Panel Report 3: Guidelines for the Diagnosis and Management of Asthma", U.S. Department of Health and Human Services, National Institutes of Health, National Heart, Lung, and Blood Instute, Aug. 28, 2007; entire report; 440 pages.
Nelson et al., "Update on the safety of long-acting β-agonists in combination with inhaled corticosteroids for the treatment of asthma," Annals of Allergy, Asthma & Immunology, 2009, 102(1):11-15.
Nelson, "Is there a problem with inhaled long-acting β-adrenergic agonists?" J Allergy Clin Immunol, 2006, 117(1):3-16.
Rowe B. H. et al: "Management of severe acute asthma in the emergency department", Current Opinion in Critical Care, vol. 17, pp. 335-341, 2011.
Silverman et al., "IV Magnesium Sulfate in the Treatment of Acute Severe Asthma," Chest, 2002, 122(2):489-497.
Spiteri et al., "Subcutaneous adrenaline versus terbutaline in the treatment of acute severe asthma," Thorax, 1988, 43:19-23.
Travers et al., "The Effectiveness of IV β-Agonists in Treating Patients With Acute Asthma in the Emergency Department : A Meta-analysis," Chest, 2002, 122(4):1200-1207.
Tsai Et Ali: "Quality of care for acute asthma in 63 US emergency departments", The Journal of Allergy and Clinical Immunology, vol. 123, No. 2, pp. 354-361, Feb. 2009.
Wheeler et al., "Theophylline versus terbutaline in treating critically ill children with status asthmaticus," Pediatr Crit Care Med, 2005 6(2):142-147.
Yanagi et al., "Asymmetric Borane Reduction of Prochiral Ketone Using Chiral Bis(a, a-diphenyl-2-pyrrolidinemethanol) Carbonate," Chem Pharm Bull, 2003, 51(2):221-223.

\* cited by examiner

*Primary Examiner* — James H Alstrum Acevedo
*Assistant Examiner* — Daniel L Branson
(74) *Attorney, Agent, or Firm* — Gilberto M. Villacorta; Photon Rao; Foley & Lardner LLP

(57) ABSTRACT

The invention provides a method of improving one or more clinical outcomes of an individual experiencing an acute respiratory attack. The acute respiratory attack may include acute reversible bronchospasm, severe acute bronchospasm, or acute exacerbation of asthma. The method includes administering to an individual suffering from an acute respiratory attack an effective amount of bedoradrine or a pharmaceutically acceptable salt thereof in combination with a standard of care (SOC) treatment regimen.

30 Claims, 3 Drawing Sheets

Heart Rate vs Time in Dogs Administered MN-221 Adjunctive to Albuterol

FEV1 denotes forced expiry volume in 1 second, ICU, intensive care unit, PaCO2, partial pressure of arterial oxygen pressure, PaO2, partial pressure of arterial oxygen, PFE, peak expiratory flow, and SaO2, arterial oxygen saturation.

TREATMENT OF ACUTE EXACERBATION OF ASTHMA AND REDUCTION OF LIKELIHOOD OF HOSPITALIZATION OF PATIENTS SUFFERING THEREFROM

CROSS-REFERENCE TO RELATED PATENT APPLICATIONS

This application is a continuation of U.S. patent application Ser. No. 12/948,545, filed Nov. 17, 2010, now abandoned, which claims priority from U.S. Provisional Application Nos. 61/262,352 and 61/392,917, filed Nov. 18, 2009 and Oct. 13, 2010, respectively, all of which are incorporated herein by reference in their entirety.

FIELD OF THE INVENTION

This invention relates to a method of treating severe episodes of asthma, preventing the manifestations of severe and long-lasting episodes of asthma from worsening, and reducing the likelihood of hospitalization (or other adverse clinical outcomes) of patients suffering from severe and long-lasting episodes of asthma, including without limitation, acute exacerbation of asthma. In particular, this therapeutic approach with MN-221 (generic name: bedoradrine) provides additional bronchodilation and improved clinical outcomes including reduced hospitalization when used adjunctively to (that is, in combination with) recognized standard respiratory care for acute asthma exacerbations (i.e., nebulized albuterol, nebulized ipratropium, corticosteroids). This invention is particularly well-suited for patients who fail to respond to this standard acute respiratory care or simply "standard of care" treatment regimen.

BACKGROUND

Acute exacerbation of asthma (AEA) or status asthmaticus is a long-lasting and severe asthma episode that is typically not responsive to bronchodilator or corticosteroid therapy. An AEA may be diagnosed, for example and without limitation, by the symptoms of dyspnea and bronchospasm. Patients often experience progressively worsening breathlessness, cough, wheezing, and chest tightness, or some combination of these symptoms of AEA.

Current standard of care (SOC) for AEA treatment relies on using low flow oxygen, inhaled β-agonists (e.g., albuterol), anticholinergics (ipratropium), and/or intravenous or oral corticosteroids (e.g., prednisone and methylprednisolone); intravenous (IV) magnesium may be included. In some countries or at some points in time, IV or subcutaneous (SC) adrenoceptor agonists (e.g., epinephrine in adults and terbutaline in children) and IV aminophylline may also be administered, but are not generally recommended at least for adults according to the current *NAEPP Asthma Guidelines* (2007). See; also, S. C. Lazarus *NEJM* Aug. 19, 2010; G. J. Browne et al. *Lancet* (1997) 349:301). Moreover, these treatments may not produce a significant clinical benefit and/or may provoke unwanted cardiovascular side-effects (e.g., tachycardia) when added to SOC. Although subcutaneous adrenalin or terbutaline in conjunction with nebulized albuterol and corticosteroid and aminophylline were reported over 20 years ago (M. A. Spiteri et al, *Thorax* (1988) 43:19-23) to provide some breathing benefit without undue side effects, such parenteral beta-agonist therapy has proven over the years to be too risky—especially from a cardiovascular liability standpoint—for limited observed benefit.

Recently, D. S. Wheeler et al. *Pediatr. Crit. Care Med.* (2005) 6:142-7 showed that terbutaline added to SOC in children with status asthmaticus did not provide a significant improvement in clinical asthma score or ICU stay. A reanalysis of data by G. J. Browne et al. *Pediatr. Crit. Care Med.* (2002) 3(2) led these authors to conclude that a single-dose intravenous salbutamol bolus in the initial treatment of children with acute severe asthma in the emergency department has the potential to shorten the duration of severe attacks and reduce overall requirements for inhaled salbutamol maintenance. However, a review conducted by A. H. Travers et al. *Chest* (2002) 122:1200-1207 of publications, which described randomized controlled trials comparing the use of IV $\beta_2$-agonists versus placebo or SOC, led these authors to conclude that "[e]vidence is lacking to support the use of IV $\beta_2$-agonists in [emergency department] patients with severe acute asthma. Moreover, the clinical benefit appears questionable, while the potential clinical risks are obvious. The only recommendations for IV $\beta_2$-agonist use should be in those patients in whom inhaled therapy is not feasible, or in the context of a controlled clinical trial comparing IV $\beta_2$-agonists with standard care vs standard care alone." Hence, there appears to be little agreement in the literature as to the potential benefits of β-agonists administered intravenously. There may also be questions surrounding the merits of intravenous administration in children versus adults, who are suffering from a acute severe asthma attack and present themselves in an emergency department setting.

Although the results of a study by Appel et al. *J. Allergy Clin. Immunol.* (1989) 84:90-98 do not clearly define the role of systemic β-agonists in the treatment of life-threatening asthma, it suggests that subcutaneous administration of epinephrine or terbutaline should be considered in patients unresponsive to continuous nebulized $\beta_2$-agonists, and in those patients unable to cooperate due to alteration of mental status or an inability to tolerate inhaled therapy. Epinephrine may also be delivered in intubated patients not responding to inhaled therapy during mechanical ventilation. Subcutaneously, 0.3-0.5 mL (1:1000) of epinephrine can be administered every 20 min. to a maximum of three doses. Terbutaline can be administered subcutaneously (0.25-0.5 mg) and is the preferred treatment in pregnant females.

Intravenous infusion of terbutaline starting at 0.05-0.10 μg/kg per min has been utilized predominantly in pediatric patients. It may be considered in the treatment of patients with no response to inhaled or subcutaneous treatment, and in whom respiratory arrest is imminent, or in patients not adequately ventilated despite optimal setting of the ventilator. A recent double blind, randomized controlled trial by Bogie et al. *Pediatric Emergency Care* (2007) 23(6) evaluated the benefit of intravenous terbutaline in 49 nonventilated children with acute severe asthma who were already on continuous high-dose nebulized albuterol. Although the use of intravenous terbutaline was associated with improvement in the clinical asthma severity score over the first 24 h, shorter use of continuous nebulized albuterol, and shorter ICU stay, the differences were not statistically significant.

The Applicants have identified novel methods for the treatment of severe asthma attacks, including AEA, especially in patients who fail to respond to current SOC. The Applicants have also discovered that bronchodilation and the reduced hospitalization of patients suffering from such attacks can be achieved by administering MN-221 or pharmaceutically acceptable salts thereof (collectively, Active Agent, as described further below). The discovery that Active Agent is particularly beneficial in treating patients suffering from an acute severe respiratory attack could not have been predicted from the clinical experience of those of ordinary skill in the art using known beta-agonists. Moreover, the Applicants' believe that their discoveries have special utility in treating an "exacerbation-prone" subset of asthmatics, who are at a higher risk of experiencing an acute exacerbation of asthma (for a discussion of this subset of asthmatics see, R. H. Dougherty *Clin. Exp. Allergy.* (2009) 39:193).

SUMMARY OF THE INVENTION

Provided herein are methods for pharmacologically treating severe and long-lasting episodes of asthma, by providing intravenous administration of a highly β2-selective adrenoceptor agonist in conjunction with a standard of care treatment regimen and thus preventing the manifestations of severe and long-lasting episodes of asthma from worsening, and reducing the likelihood of hospitalization of patients suffering from severe and long-lasting episodes of asthma, including without limitation, acute exacerbation of asthma. Also provided herein are methods for selecting patients that are likely or unlikely to undergo such treatment.

In one aspect, the present invention provides a method of treating AEA, comprising administering an effective amount of the Active Agent to a patient in need of such treatment. In certain other aspects and embodiments, the invention also provides novel methods of reducing the likelihood of hospitalization (e.g., a reduced hospitalization rate or a reduced stay in an intensive care unit) and/or worsening of one or more manifestations of AEA in a patient suffering from AEA comprising administering an effective amount of the Active Agent to such patient. In other aspects, other methods of the present invention comprise determining that a patient is suffering from a long-lasting and severe asthma episode that is not responsive to initial standard of care treatment and administering to the patient an effective amount of the Active Agent. In a preferred embodiment, the Active Agent is administered parenterally, more preferably, intravenously.

The Active Agent (MN-221 a/k/a bedoradrine or its pharmaceutically acceptable salts) administered intravenously allows it to distribute and partition into the congested lung tissue of AEA patients and allow bronchodilation without undue cardiovascular side effects. Table 1, below, provides an example of the adrenoceptor action profile for MN-221 determined experimentally:

TABLE 1

Adrenoceptor Action Profile for MN-221

| Study | System | μM β1 | β2 | β1/β2 | Comment |
|---|---|---|---|---|---|
| Cerep 14320 | Competitive Binding ($IC_{50}$) | 11.8 | 0.27 | 42 | HEK (Human β1), CHO (Hu β2) |
| | cell bioassay (EC50 cAMP accum.) | >50 | 0.013 | >3000 | HEK (Human β1), CHO (Hu β2) |
| Cerep 13271 | ex vivo Organ bioassay (est EC39*, EC50) | ~1* | 0.028 | 36 | GP Rt atrium (% isoprot); GP carbachol-tx trachea (% salbut) a partial agonist. Emax = 39% |

*= $EC_{39}$ i.e., 39% of isoproterenol maximum response

In another aspect, the present invention provides a method of treating AEA by administering an effective amount of the Active Agent to a patient in need of such treatment wherein the AEA or one or more manifestations of the AEA are non-responsive or substantially non-responsive to treatment with SOC. In another aspect, the present invention provides a method of treating a severe and long-lasting episode of asthma by administering an effective amount of the Active Agent to a patient in need of such treatment, wherein the severe and long-lasting episode of asthma or one or more manifestations of it are non-responsive or substantially non-responsive to treatment with SOC. Within the aspects and embodiments of the present invention, in one embodiment, the Active Agent administered is MN-221 or pharmaceutically acceptable salts thereof. For example and without limitation, patients suffering from AEA (for example, those admitted to an emergency room because of an acute exacerbation of asthma), who were not responsive to SOC, were treated with MN-221 (in addition to having been treated with SOC) and their treatment outcomes compared with those of similar patients treated with SOC only (or SOC plus a placebo). The hospitalization rate among those patients who were treated with SOC only, was 54 percent (7 of 13, roughly half), compared to a hospitalization rate of 25 percent (4 of 16, roughly a quarter) among those patients who were treated with MN-221 and with SOC, demonstrating improved breathing ability (see, FIG. 1) and about a 50 percent reduction in hospitalization rate among AEA patients who were also treated with MN-221. Thus, the invention also provides novel methods of reducing the likelihood of hospitalization of patients suffering from AEA, who are non-responsive to SOC. In one embodiment of the invention, the likelihood of hospitalization of a patient suffering from an acute exacerbation of asthma treated with MN-221 alone or in combination with SOC falls to substantially less than half or fifty percent, preferably, to about a quarter (or twenty-five percent) of all patients suffering from an acute respiratory attack.

A DESCRIPTION OF PREFERRED EMBODIMENTS

Figure 1:
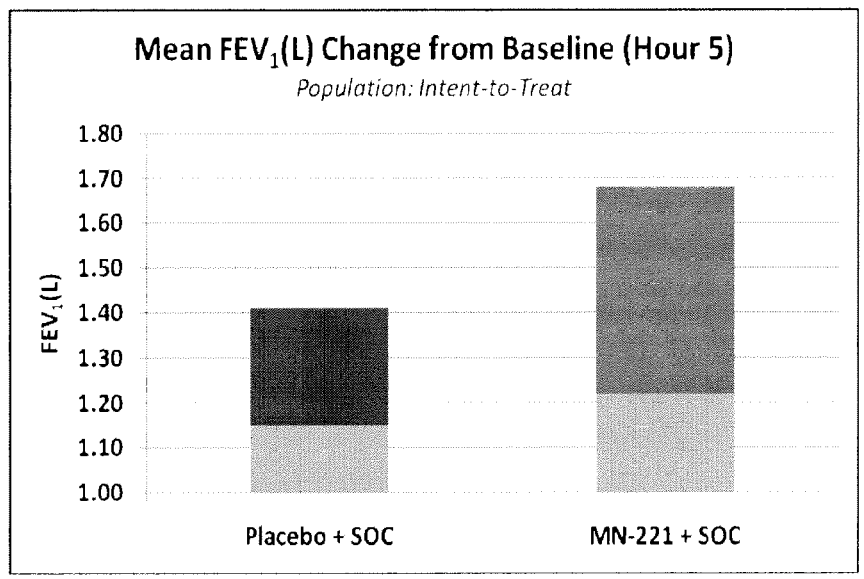
FIG. 1 shows the improvement over baseline of $FEV_1$ between patients being treated with placebo and SOC versus patients being treated with a combination of SOC and MN-221.

The invention provides a method of improving one or more clinical outcomes of an individual experiencing an acute respiratory attack. The acute respiratory attack is severe and usually requires that the individual present himself or herself to an emergency department (i.e., emergency room) of a hospital. An acute respiratory attack may include an acute reversible bronchospasm, a severe acute bronchospasm, or an acute exacerbation of asthma. The inventive method comprises administering to an individual suffering from an acute respiratory attack an effective amount of bedoradrine or a pharmaceutically acceptable salt thereof in combination with a standard of care (SOC) treatment regimen. The bedoradrine or a pharmaceutically acceptable salt thereof can be administered after administration of the SOC treatment regimen, contemporaneously with the SOC treatment regimen, or before administration of the SOC treatment regimen. A SOC treatment regimen comprises administration of one or more β-agonist bronchodilators, one or more anti-cholinergic drugs, one or more corticosteroids, or combinations thereof. The SOC treatment regimen may also includes the administration of magnesium.

Typically, the one or more β-agonist bronchodilators, or one or more anti-cholinergic drugs are administered by inhalation, injection, or intravenous infusion. The one or more β-agonist bronchodilators may be selected from albuterol, bitolterol, levalbuterol, pirbuterol, epinephrine, terbutaline, formoterol, or salmeterol, whereas the one or more anti-cholinergic drugs may, in turn, be selected from ipratropium or tiotropium. The one or more corticosteroids may be selected from prednisone, methylprednisolone, or prednisolone.

The bedoradrine or a pharmaceutically acceptable salt thereof may be administered by any suitable route, but more preferably, intravenously, orally, or by inhalation. The amount of bedoradrine or a pharmaceutically acceptable salt thereof administered to an individual typically falls in the range of 100 to 5,000 μg. More preferably, about 500 to about 1,500 μg of bedoradrine or a pharmaceutically acceptable salt thereof is administered intravenously over a period of about 5 to about 120 minutes. The invention provides for one or more improved clinical outcomes. Such improved clinical outcomes may include an increase in $FEV_1$, a reduction in likelihood of hospitalization, an improvement in dyspnea scores, a reduction in incidence of intubation, a reduction in length of stay in an intensive care unit and an improvement in self-ambulation unaccompanied by respiratory distress. Usually, the $FEV_1$ improves by 5% or more, 10% or more, or 15% or more.

The Applicants have found that the likelihood of hospitalization of an individual receiving the claimed combination (i.e., MN-221 plus SOC) treatment is reduced compared with an individual receiving only the SOC treatment regimen. (Whenever the term "placebo" is mentioned in this disclosure in combination with SOC, what it is meant is that an individual simply continues to receive the SOC treatment regimen and no test drug, such as MN-221 or a pharmaceutically acceptable salt thereof.) Following the teachings of the invention, the likelihood of hospitalization of an individual receiving the claimed combination treatment is reduced to about 25% or less, about 20% or less, or about 15% or less. An individual who will tend to benefit from the administration of bedoradrine or its pharmaceutically acceptable salt is an individual who is not responsive to an inhaled β-agonist bronchodilator, most typically albuterol. Such an individual is likely to experience an improvement from the acute respiratory attack for about 1 hour or more, about 2 hours or more, about 3 hours or more, about 4 hours or more, about 5 hours or more, about 6 hours or more, or about 8 hours or more after the claimed combination treatment. The nature of the improvement may typically manifest itself in the form of an improvement in $FEV_1$ (L), $FEV_1$ (% predicted), PEFR, arterial blood oxygen saturation, respiratory rate, or combinations thereof after the claimed combination treatment, unaccompanied by one or more clinically observable adverse events. Such clinically observable adverse events may include, but are not limited to, an increased heart rate, an increased blood glucose, tremor, headache, palpitations, or a jittery feeling.

The invention is also directed to a method of alleviating one or more negative effects of an acute respiratory attack selected from the group consisting of acute reversible bronchospasm, severe acute bronchospasm and acute exacerbation of asthma, comprising administering to a patient, who has been diagnosed as suffering from either acute reversible bronchospasm, severe acute bronchospasm, or acute exacerbation of asthma, an effective amount of bedoradrine or a pharmaceutically acceptable salt thereof. More specifically, the patient suffers from an acute, severe asthma attack, otherwise known as an acute exacerbation of asthma. Target patients of the invention will be those who typically fail to respond to an SOC treatment regimen. In the Applicants' hands, such a patient experiences improved $FEV_1$ relative to the patient's pre-treatment $FEV_1$ and the improved $FEV_1$ persists on average for at least about 6 hours at a level that is about 50% or more of a peak effect. A preferred daily amount of bedoradrine or a pharmaceutically acceptable salt thereof administered to a patient falls in the range of about 300 to 1500 μg. Applicants believe that the invention will find a special utility in treating persons who belong to an exacerbation-prone subset of asthmatics, who are typically at high risk of suffering from an acute exacerbation of asthma.

Other preferred embodiments of this invention will become evident from a detailed study of this disclosure. Applicants' wish to incorporate by reference herein the entirety of the disclosures of any patent or non-patent reference cited anywhere in this disclosure.

DETAILED DESCRIPTION OF THE INVENTION

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

"Active Agent" refers to an agent selected from the group consisting of MN-221, the free base form of MN-221, other pharmaceutically acceptable salts of the MN-221 free base (e.g., organic or inorganic acid addition salts), their pharmaceutically acceptable metabolites (e.g., a carboxylic acid), and pharmaceutically acceptable salts of their metabolites.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"Effective amount" of a drug is an amount of a drug that, when administered to a patient with AEA, will have the intended therapeutic effect, e.g., alleviation, amelioration, palliation or elimination of one or more manifestations of AEA in the patient. The full therapeutic effect does not necessarily occur by administration of one dose (or dosage), and may occur only after administration of a series of doses. Thus, a therapeutically effective amount may be administered in one or more administrations.

"First line treatment" refers to a treatment intended as an initial treatment of AEA. When first line treatment fails or is inadequate, subsequent treatments referred to as second line treatment and third line treatment may be used.

"Manifestation" of AEA refers to a symptom, sign, physiological state (e.g., heart rate, cough, shortness of breath and/or difficulty of breathing, hypoxia, or anxiety associated with inability to breathe), or report (e.g., $FEV_1$, $FEV_1\%$, or PEFR) characteristic of a patient with AEA.

"MN-221" refers to the sulfate salt of formula: acetamide, N,N-dimethyl-2-[[(7S)-5,6,7,8-tetrahydro-7-[[(2R)-2-hydroxy-2-[4-hydroxy-3-(2-hydroxyethyl)phenyl]ethyl]amino]-2-naphthalenyl]oxy], sulfate (also known as bis[2-[[(7S)-7-[[(2R)-2-hydroxy-2-[4-hydroxy-3-(2-hydroxyethyl)phenyl]ethyl]amino]-5,6,7,8-tetrahydronaphthalen-2-yl]oxy]-N,N-dimethylacetamide] sulfate or (−)-bis(2-{[(2S)-2-({(2R)-2-hydroxy-2-[4-hydroxy-3-(2-hydroxyethyl)phenyl]ethyl}amino)-1,2,3,4-tetrahydronaphthalen-7-yl]oxy}-N,N-dimethyl-acetamide) monosulfate).

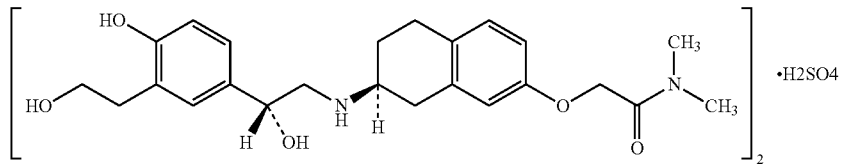

MN-221 is synthesized according to methods reported in literature. See, e.g., the references Yanagi et al. *Chem. Pharm. Bull.* (Tokyo) (2003) 51(2):221-23 and U.S. Pat. No. 6,133,266. Without being bound by mechanism, MN-221 may possess a greater selectivity for the human $\beta_2$ receptors than $\beta$-agonists commonly used to treat acute exacerbation of asthma (i.e., albuterol, levalbuterol, terbutaline). In addition, MN-221 may act as a full agonist at $\beta_2$-adrenergic receptors and a partial agonist at the $\beta_1$-adrenergic receptor. The MN-221 may provide bronchodilation with a reduced risk of cardiovascular complications (e.g., tachycardia, arrhythmia). An example of a pharmaceutically acceptable metabolite of MN-221 includes, without limitation, a metabolite resulting from the hydrolysis of the amide moiety. A carboxylic acid, representative of a hydrolysis product, is described in U.S. Pat. No. 6,136,852, the disclosure of which is incorporated herein by reference.

"Patient," "individual," or "subject" refers to humans.

"Reduction" of a symptom or symptoms (and grammatical equivalents of this phrase) means decreasing of the severity or frequency of the symptom(s), or elimination of the symptom(s). A reduction in a likelihood of hospitalization means a lowering of a frequency of hospitalization or a reduction in a hospitalization rate, for example, from a 50% rate to a 25% rate, or lower, such as 15% or 10%.

"Treating" a condition or patient refers to taking steps to obtain beneficial or desired results, including clinical results. For purposes of the various aspects and embodiments of the present invention, beneficial or desired clinical results include, but are not limited to, reduction, alleviation or amelioration of one or more manifestations of or negative effects of an acute respiratory attack (e.g., AEA), improvement in one or more clinical outcomes, diminishment of extent of disease, delay or slowing of disease progression, amelioration, palliation or stabilization of the disease state, and other beneficial results described herein.

Various aspects and embodiments of the invention are described hereinafter. It should be noted that the specific embodiments are not intended as an exhaustive description of the invention or as a limitation on the scope of the invention. One aspect or embodiment, described in conjunction with a particular embodiment of the present invention is not necessarily limited to that embodiment and can be practiced with any other embodiment(s) of the invention.

In one aspect, the present invention provides a method of treating AEA, comprising administering an effective amount of the Active Agent to a patient in need of such treatment. In certain other aspects and embodiments, the invention also provides novel methods of preventing hospitalization, or reducing a rate of hospitalization and/or worsening of one or more manifestations of AEA in a patient suffering from AEA comprising administering an effective amount of the Active Agent to the patient in need of such prevention. In other aspects, other methods of the present invention comprise determining that a patient is suffering from a long-lasting and severe asthma episode that is not responsive to initial standard of care treatment and administering to the non-responsive patient an effective amount of the Active Agent.

In another aspect, the present invention provides a method of treating AEA by administering an effective amount of the Active Agent to a patient in need of such treatment wherein the AEA or one or more manifestations of the AEA are non-responsive or substantially non-responsive to treatment with SOC. One of skill in the art, upon reading this disclosure will be able to determine, based on the severity, improvement, and worsening of the manifestations of AEA, whether a patient is substantially or completely unresponsive to treatment with SOC. In another aspect, the present invention provides a method of treating a severe and long-lasting episode of asthma by administering an effective amount of the Active Agent to a patient in need of such treatment, wherein the severe and long-lasting episode of asthma or one or more manifestations of it are non-responsive or substantially non-responsive to treatment with SOC.

In another aspect, the present invention provides methods of preventing hospitalization, or reducing the likelihood of hospitalization, of a patient suffering from an AEA, comprising administering to a patient, who has been diagnosed as suffering from AEA, an effective amount of the Active Agent. In one embodiment, the patient is suffering from a long-lasting and severe asthma episode that is not responsive to initial bronchodilator, or corticosteroid, or combination therapy thereof. The long-lasting and severe asthma episodes include but is not limited to persistent cough secondary to asthma, shortness of breath and/or difficulty of breathing secondary to asthma, hypoxia secondary to asthma, or anxiety associated with inability to breathe or shortness of breath that is not responsive to initial bronchodilator or corticosteroid or combination therapy thereof.

Within the various aspects and embodiments of the present invention provided herein, in one embodiment, the Active Agent administered is MN-221.

In related embodiments, the patient treated shows as a symptom of AEA, a decreases in respiratory rate. In yet another embodiment, the patient has been admitted to an emergency room. In other related embodiments, only about 20% to about 30% and only about 40% to about 50% of the patients treated with the Active Agent are hospitalized. In yet another embodiment, the patient in accordance to the present invention refers to patent that is not responsive to albuterol or methylprednisolone therapy, alone or in combination with one another.

In yet another embodiment, the present invention provides methods of improving $FEV_1$, $FEV_1\%$, peak expiratory flow rate (PEFR) or arterial blood oxygen saturation of a patient suffering from AEA, comprising: administering to the patient an effective amount of the Active Agent. $FEV_1$ refers to the amount of air which can be forcibly exhaled from the lungs in the first second of a forced exhalation, and may be measured by spirometry. $FEV_1\%$ refers to $FEV_1$ expressed as a percentage of the vital capacity, and is an index for assessing and quantifying airflow limitations. Vital capacity refers to the volume change of the lung between a full inspiration and a maximal expiration. In a related embodiment, the present invention provides methods of improving $FEV_1$, $FEV_1\%$, PEFR, or arterial blood oxygen saturation, or decreasing a respiratory rate, of a patient suffering from AEA, comprising administering to a patient, who has been diagnosed as suffering from AEA, an effective amount of the Active Agent. Typically, an improvement in $FEV_1$ or $FEV_1\%$ or PEFR or arterial blood oxygen saturation, or a decrease in respiratory rate, is achieved without observing clinically meaningful changes in heart rate, systolic, or diastolic blood pressure, or serum potassium when such administration is coupled to other standard of care treatments for acute exacerbation of asthma.

In another embodiment, the improved $FEV_1$ is determined in comparison with a pre-treatment $FEV_1$. In another embodiment, the improved $FEV_1$ persists on average for at least about 5 hours at a level that is about 50% or more of a peak effect. The term "peak effect," as used herein, refers to the highest, post-treatment percentage improvement in average $FEV_1$. In another embodiment, the improved $FEV_1$ persists for about 2 hours to about 12 hours, about 4 hours to about 10 hours, and for about 6 hours to about 8 hours, at a level that is about 50%, about 60%, about 70%, or more of the maximum average $FEV_1$ increase observed after initiating administration of the Active Agent.

An example of improved $FEV_1$ of patients suffering from an acute exacerbation of asthma attack who were treated with a combination of MN-221 and SOC is graphically shown in FIG. 1. The graphical representation also includes changes from baseline $FEV_1$ in patients receiving only SOC (that is, "Placebo+SOC," which means patients received continuous SOC only; "MN-221+SOC" means patients received a combination of MN-221 and SOC). The data is tabulated in Table 2.

TABLE 2

Percent Change in $FEV_1$ Liters at Hour 5 from Start of Infusion (Population: Intent-to-Treat)

| | Baseline | Change in Liters | At 5 Hours after start of |
|---|---|---|---|
| Placebo + SOC | 1.15 | 0.26 | 1.41 |
| MN-221 + SOC | 1.22 | 0.46 | 1.68 |

As noted above, when MN-221 was combined with standard of care in patients with acute exacerbations of asthma, an observed clinical benefit was reduced hospitalization. Moreover, additional bronchodilation was observed as measured by $FEV_1$ as depicted in Table 2. The placebo plus SOC group (that is, the continuous SOC group) experienced a 23% positive change in $FEV_1$ value. The MN-221 plus SOC group experienced a 38% positive change in $FEV_1$ value, however. The mean $FEV_1$ (L) change from baseline was 200 mL (0.20 L) greater in the MN-221+SOC dose group versus the Placebo+SOC dose group. This additional bronchodilation benefit in the MN-221 dose group is depicted graphically in FIG. 1.

Figure 2:
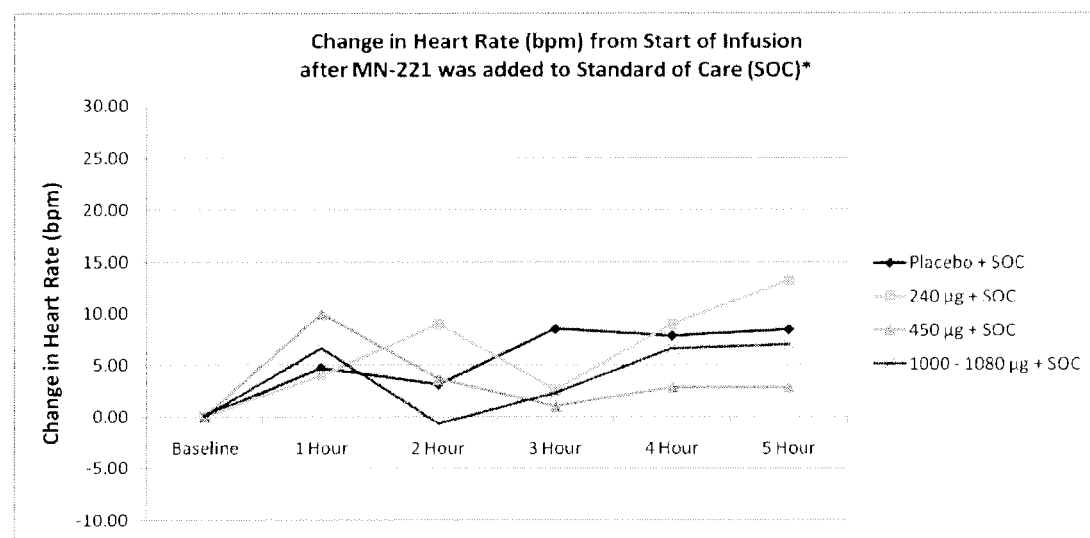
FIG. 2 shows the absence of an adverse change in heart rate for patients receiving placebo and SOC versus patients receiving a combination of MN-221 and SOC.
Figure 3:
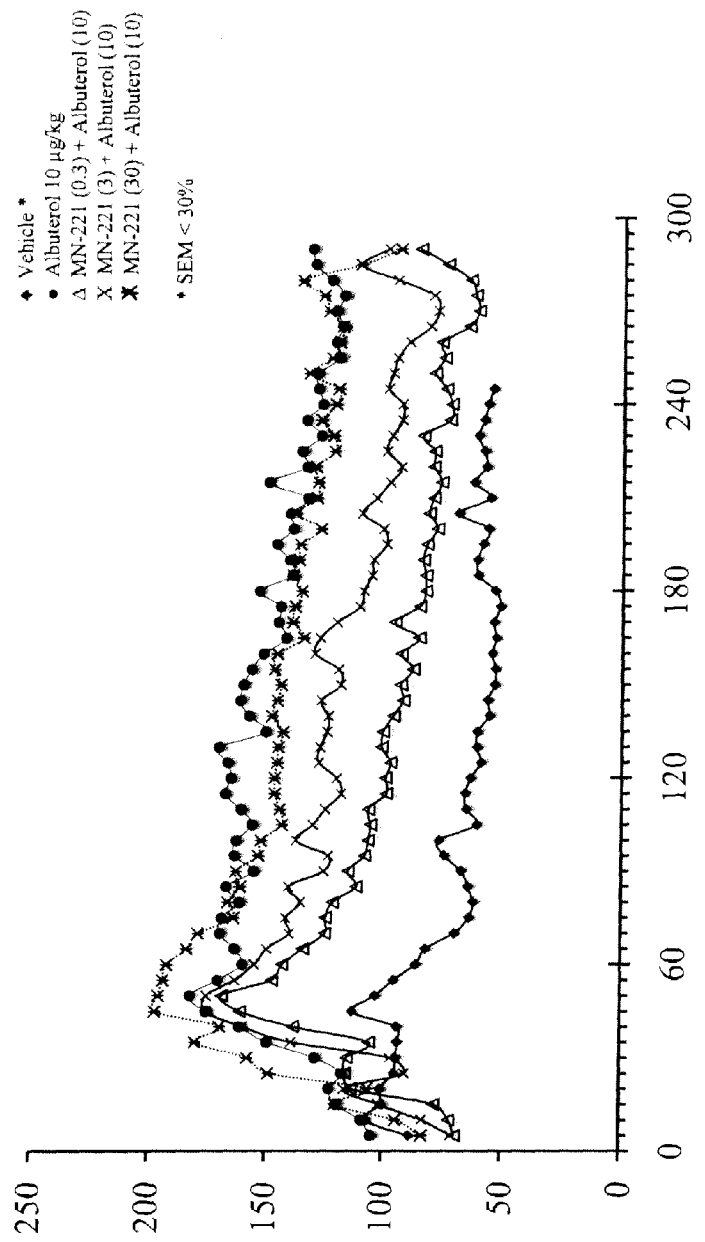
FIG. 3 depicts the heart rate of dogs receiving vehicle, albuterol and three dosage levels of MN-221 adjunctive to albuterol.

Importantly, the observed clinical benefits (e.g., reduction in hospitalization rate, additional bronchodilation, etc.) occurred in the absence of significant heart rate increase, thus supporting safety and providing unexpected results over the use of other β-agonists. The absence of a significant change in hear rate is depicted in FIG. 2.

In another aspect, the present invention provides a method of treating a patient suffering from an acute exacerbation of asthma comprising administering an effective amount of a pharmaceutical composition comprising a solution of MN-221 or a solution of a pharmaceutically acceptable salt of MN-221 thereby treating the patient. In another embodiment, the patient experiences an improved $FEV_1$, compared to a pre-treatment $FEV_1$. In another embodiment, the improved $FEV_1$ persists on average for at least about 5 hours at a level that is about 50% or more of a peak effect. In another embodiment, the improved $FEV_1$ persists for about 2 hours to about 12 hours, about 4 hours to about 10 hours, and for about 6 hours to about 8 hours, at a level that is about 50%, about 60%, about 70%, or more of the maximum average $FEV_1$ increase observed after initiating administration of the pharmaceutical composition.

In a preferred embodiment, the Active Agent is administered in combination with administration of SOC. Thus, the Active Agents is administered to an AEA patient in combination with other agents or procedures intended to treat AEA, ameliorate symptoms of AEA, potentiate the effects of the Active Agents, or provide other therapeutic benefit. Administration of an agent "in combination with" includes parallel administration (administration of both the agents to the patient over a period-of time), co-administration (in which the agents are administered at approximately the same time, e.g., within about a few minutes to a few hours of one another, such as, administration of MN-221, and albuterol, ipratropium, and/or prednisone or prednisolone on same days), and co-formulation (in which the agents are combined or compounded into a single dosage form suitable for oral, inhaled or parenteral administration).

In other embodiments, the SOC thus administered in combination comprises one or more of a β-agonist, anti-cholinergic agent, and a corticosteroid. In another embodiment, the β-agonist is an inhaled β-agonist. In another embodiment, the β-agonist is albuterol. In another embodiment, the albuterol is administered at a rate of from about 5 mg/hr to about 5 mg once every 20 minutes. In another embodiment, the albuterol administration is intermittent or continuous. In another embodiment, the anticholinergic agent is ipratropium. In yet another embodiment, the β-agonist or the anticholinergic agent is administered employing a nebulizer or an MDI (metered dose inhaler). In another embodiment, the corticosteroid is prednisone or methylprednisolone. In another embodiment, the corticosteroid is administered orally or parenterally.

In another aspect, the present invention provides a method of treating a patient suffering from an acute exacerbation of asthma comprising administering an effective amount of a pharmaceutical composition comprising a solution of MN-221 or a solution of a pharmaceutically acceptable salt of MN-221 and administering an effective amount of an inhalable pharmaceutical composition comprising a beta-agonist other than MN-221 or a pharmaceutically acceptable salt of the beta-agonist, thereby treating the patient. In another embodiment, the beta-agonist other than MN-221 is albuterol.

In another embodiment, the solution of MN-221 is administered intravenously. In another embodiment, the MN-221 is administered in a daily amount of about 600 µg to about 1200 µg. In another embodiment, the effective amount of the pharmaceutical composition comprising a solution of MN-221 or a solution of a pharmaceutically acceptable salt of MN-221 is administered over a period of about 15 minutes to about 2 hours.

In another aspect, the present invention provides a method of treating a patient suffering from an acute exacerbation of asthma comprising:
(a) administering an agent or a therapy that is a standard of care (SOC);
(b) determining if the patient exhibits a positive or negative response to said step (a);
(c) discharging the patient if the patient exhibits a positive response to said step (a);
(d) administering an effective amount of an injectable pharmaceutical composition comprising a solution of MN-221 or a solution of a pharmaceutically acceptable salt thereof, if the patient exhibits a negative response to said step (a);
(e) determining if the patient exhibits a positive or negative response to said step (d);
(f) discharging the patient if the patient exhibits a positive response to said step (d); and
(g) admitting the patient to a hospital if the patient exhibits a negative response to said step (d). In another embodiment, the patient discharged in step (f) remains symptom-free on average for at least about 3 hours after discharge. In another embodiment, the patient discharged in step (f) remains symptom-free on average for at least about 5 hours after discharge.

Figure 4:
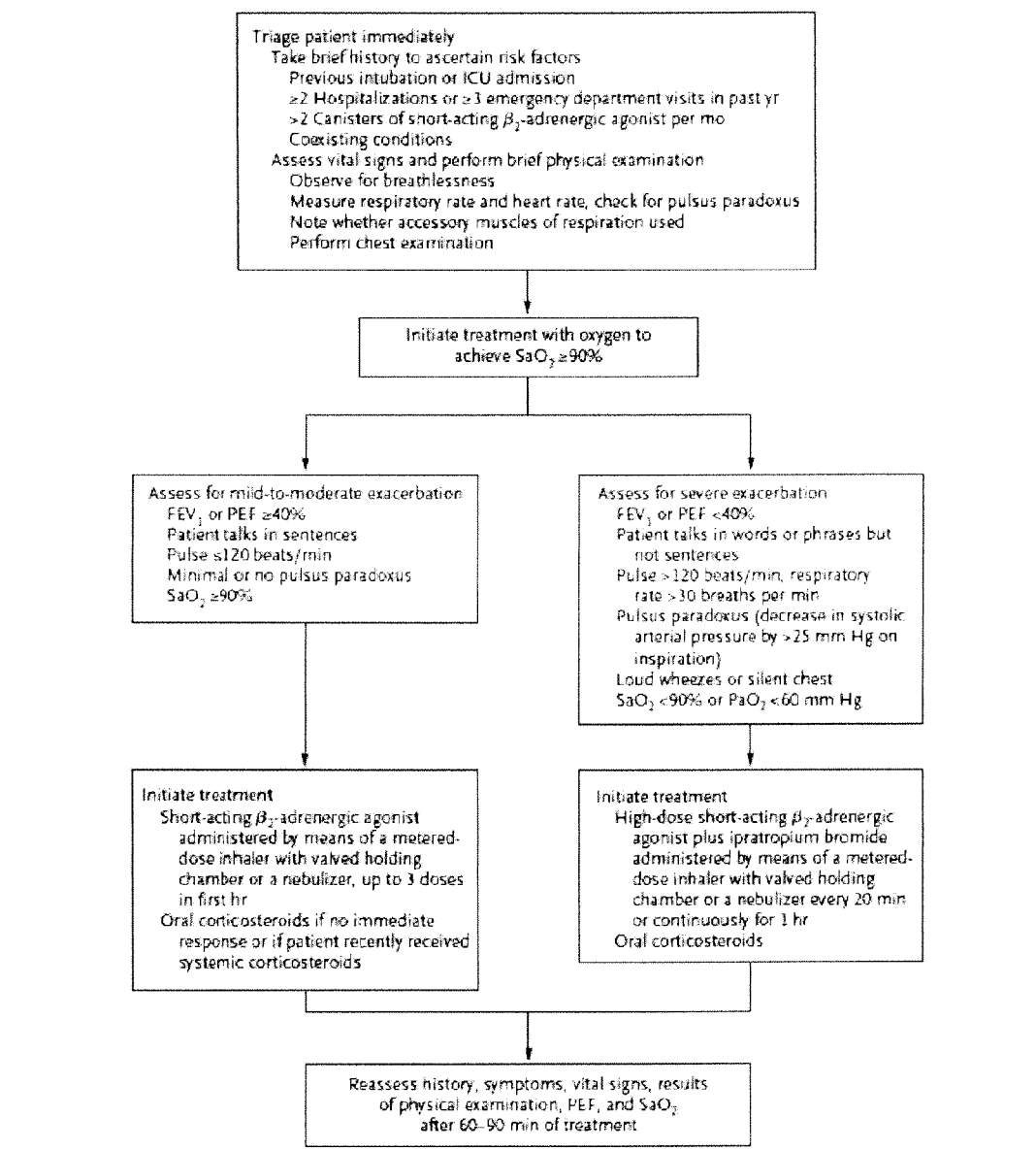
FIG. 4 provides a flow chart of an exemplary SOC treatment regimen for a patient presenting to an emergency room likely suffering from an acute respiratory attack.

A potential scenario for admission, diagnosis and treatment of a patient suffering from an acute respiratory attack is depicted in the flow diagram, shown in FIG. 4 (See, Lazarus, S. C., in *N. Engl. J. Med.* (2010) 363:755-764.)

In other embodiments, the treatment methods provided herein are part of a first line treatment. In other embodiments, the treatment methods provided herein are part of a second line treatment or part of a third line treatment.

In another aspect, the present invention provides a method of selecting a patient suffering from acute exacerbation of asthma as likely or unlikely to be suitable for treatment comprising administration of MN-221 or a pharmaceutically acceptable salt thereof, the method comprising:
administering to the patient a standard of care (SOC), and determining the $FEV_1$ of the patient,
wherein, if the $FEV_1$ is ≦about 55% of the predicted value, the patient is likely to undergo treatment comprising the administration of MN-221 or a pharmaceutically acceptable salt thereof, and
if the $FEV_1$ is >55% of the predicted value, the patient is unlikely to undergo treatment comprising the administration of MN-221 or a pharmaceutically acceptable salt thereof, thereby selecting the patient.

In certain embodiments, if the $FEV_1$ is ≦about 50%, ≦about 40%, ≦about 25% of the predicted value, the patient is likely to undergo treatment comprising the administration of MN-221 or a pharmaceutically acceptable salt thereof As used herein, the "predicted value" of $FEV_1$ is a measure of $FEV_1$ which may be calculated following well known methods based on age, height, gender and race, and observed FVC, $FEV_1$ and FEF25-75% values. As used herein, FVC refers to forced vital capacity, which is the total volume of air that can be exhaled from the lungs during a forced expiration following a maximal inspiration. As used herein, FEF25-75% refers to forced expiratory flow 25-75%, which is the average expired flow over the middle half of the FVC maneuver and may be considered a sensitive measure of small airways narrowing.

In another embodiment, the patient is likely to be suitable for treatment comprising administration of MN-221 or a pharmaceutically acceptable salt thereof. In another embodiment, the method further comprising administering to the patient an effective amount of a pharmaceutical composition comprising a solution of MN-221 or a solution of a pharmaceutically acceptable salt of MN-221, thereby treating the acute exacerbation of asthma. In another embodiment, the MN-221 is administered in an amount of about 600 µg/patient to about 1200 µg/patient. In another embodiment, the effective amount of the pharmaceutical composition is administered over a period of about 15 minutes to about 2 hours. In another embodiment, the beta-agonist other than MN-221 is albuterol.

In certain embodiments, the patient may be selected from the following pool of potential patient for practicing the methods of the present invention: they may be male or female; may have self-reported history of physician-diagnosed and treated asthma for ≧3 months; and may have a diagnosis of an acute exacerbation of asthma upon presentation at the ED as defined by dyspnea, evidence of bronchospasm, and by a known history of asthma. Upon presentation to the ED, such patients may have undergone: a brief physical examination that includes checking vital signs and auscultation, and assessing accessory respiratory muscle usage and the level of dyspnea the patient is experiencing; spirometry to measure the patient's $FEV_1$ (expressed as % of predicted); administration of supplemental oxygen to maintain oxygen saturation as measured by pulse oximetry of ≧90%; administration of two doses of inhaled beta2-agonist (e.g., and without limitation, about 5 mg of albuterol) via nebulizer (each dose given sequentially once a hour or about once every 20 minutes), simultaneously with two doses of an inhaled anti-cholinergic agent (e.g., and without limitation, 0.5 mg ipratropium) via nebulizer (each dose given sequentially once about every 20 minutes) and a dose of corticosteroid of about 60 mg given orally (prednisone) or intravenously (methylprednisolone). The number and amount of SOC administered may be altered as will be apparent to one skilled in the art. The suitable patient may also have an $FEV_1$≦55% within about 10 minutes of completing the SOC treatment as described immediately above; have ECG with no dysrhythmias (except sinus tachycardia); and have no clinical or electrocardiographic signs of ischemic heart disease.

The SOC administered as part of selecting patients and as part of treating patients, in accordance to the present invention, may include standardized care consistent with the National Asthma Education and Prevention Program (NAEPP) guidelines. Upon presentation to the ED for assessment and treatment for an acute exacerbation of asthma, the patient may receive standardized care consistent with the National Asthma Education and Prevention Program (NAEPP) guidelines. Once the patient has received the standardized initial treatment regimen and has been assessed for response to that treatment (signs and symptoms of acute asthma exacerbation), one or more of a 12-lead ECG, a dyspnea index scale assessment, and spirometry may be performed. If the patient's $FEV_1$ is ≦55% of predicted the patient may be suitable for treatment in accordance with the present methods. Throughout the screening process, the patient may continue to receive the appropriate medical care consistent with the NAEPP guidelines for the intended treatment of acute exacerbations of asthma.

In certain embodiments, during the treatment period, the patient may continue to receive one or more of the following standard treatments and assessments until the patient's $FEV_1$ reaches ≧about 70%, of predicted. Such standard treatments and assessments include: assessment of the patient's signs and symptoms; completion of a dyspnea index scale; supplemental oxygen to maintain oxygen saturation as measured by pulse oximetry of ≧about 90%; albuterol (2.5 mg) via nebulizer given hourly or once every 20 minutes; ipratropium (0.5 mg) via nebulizer may be given every hour; spirometry completed within 10 minutes of nebulizer treatments; followed by, reassessment of signs and symptoms.

In certain embodiments, if the patient does not improve to $FEV_1$≧70% of predicted during the treatment period, the patient may continue to receive further treatment including hospital admission. Safety, efficacy and PK parameters may be monitored throughout the treatment period. An initial 24-hour follow-up visit may be completed to evaluate the patient's health status as well as for safety and PK parameters. A second follow-up contact may be completed by telephone seven days post-randomization for safety purposes and to evaluate the patient's health status, The occurrence of clinical signs, symptoms, laboratory abnormalities, ECG abnormalities suggesting toxicity, or results of efficacy analyses ($FEV_1$, dyspnea index scale), may result in a decision to modify the proposed planned dose escalations, to repeat a dose level, or to not evaluate any additional dose(s) of MN-221.

One or more of the following outcomes may be used to determine the usefulness of the present methods. They include: a change of $FEV_1$ expressed as percent of predicted after two doses of albuterol (e.g., and without limitation at about 2.5 mg to about 5 mg each) and ipratropium (e.g., and without limitation at about 0.5 mg each) when compared to $FEV_1$ 2 hour after ("hour 2") the start of MN-221 infusion; the safety, tolerability, and pharmacokinetic profile of MN-221 when administered after two doses of albuterol (e.g., and without limitation at about 5 mg each) and ipratropium (e.g., and without limitation at about 0.5 mg each) in patients with acute exacerbation of asthma; a measurement of $FEV_1$% of predicted at time points other than about hour 2 (e.g., and without limitation at about hour 3, about hour 4, about hour 5, about hour 6, about hour 7, and about hour 8); a measurement of $FEV_1$ (L); a measurement of PEFR (L/sec); a measurement of PEFR, expressed as percent (%) of predicted; and a measurement of dyspnea index scale. As used herein, e.g., "hour 2" refers to 2 hours after administration of MN-221, and incldes 2 hours after stopping administration of MN-221. The various aforementioned outcomes may be measured at time intervals of about hours 1, 2, 3, 4, 5, 6, 7, 8, and 24; additionally the dyspnea index scale may be measured at about day 8 also. One or more of the following outcomes may also be used to determine the usefulness of the present methods: a measurement of the number of albuterol treatments in combination with MN-221 to achieve $FEV_1$≧50%, ≧60%, and ≧70%; a measurement of time to achieve FEV1≧50%, ≧60%, and ≧70%; a measurement of the hospital admission rate; a measurement of the length of stay in hospital (in hours); and a measurement of the intensive care unit (ICU) admission rate.

In another embodiment, the standard of care comprises one or more of about 2.5 mg to about 5 mg of albuterol administered by a nebulizer, or MDI about 1 mg of ipratropium administered by a nebulizer, or MDI; about 50 mg of prednisone administered orally, or about 50 mg of methylprednisolone administered intravenously; and about 2 gm of magnesium sulfate administered intravenously.

In certain other embodiments within the various aspects and embodiments of the present invention, the Active Agent is administered i.v. in a daily amount of about 2400 μg (or 2.4 mg), about 1200 μg, about 1000 μg, about 800 μg, about 600 μg, about 450 μg, about 250 μg. In other embodiments, the Active Agent is administered in a single-dosed amount of about 200 μg to about 2000 μg.

In certain embodiments within the various aspects and embodiments of the present invention, the Active Agent is administered by infusion. In one embodiment, the infusion is performed at a rate of about 3 μg (μgm or μg)/minute to about 60 μg/min; about 6 μg/minute to about 30 μg/minute; about 12/minute to about 15 μg/minute; about 7 μg/minute to about 18 μg/minute; about 9 μg/minute; about 13 μg/minute; and about 16 μg/minute.

In yet another embodiment, the patient is administered intravenously for 15 minutes at about 40 μg/min and then about 45 minutes at about 13 μg/min. In yet another embodiment, in accordance with the invention methods, the patients are those who have been admitted to an emergency room. In still other embodiments, the patient may be treated in the vicinity of where the acute exacerbation of asthma occurred, or while being transported to a hospital (e.g., in an emergency rescue vehicle or ambulance).

In yet another embodiment, in accordance with the invention methods, the patient is administered an initial amount of the Active Agent in the range of about 3 μg/kg patient (or about 200 μg per patient) to about 60 μg/kg patient (or about 4 mg per patient). The Active Agent may be administered over a period of about 1 minute to up to about 4 hours.

In certain embodiments within the various aspects and embodiments of the present invention, the Active Agent is administered for a period of time up to about 3 hours (h), up to about 2 h, up to about 1 h, up to about 45 min, up to about 30 min, and up to about 15 min. The Active Agent may be administered at various rates of administration, for various periods of time.

In some embodiments, the composition is administered as a formulation suitable for parenteral routes of administration, such as intravenous injection or infusion, intramuscular, percutaneous, and subcutaneous administration. For parenteral application, particularly suitable are solutions, preferably oily or aqueous solutions, as well as suspensions, emulsions, or implants, including suppositories.

In a related embodiment, the intravenous formulation comprises approximately 0.20 mg to about 20 mg; or alternatively about 0.20 mg to about 10 mg; or alternatively about 0.20 mg to about 5 mg; or alternatively about 0.20 mg to about 3 mg; or alternatively about 0.20 mg to about 2 mg; or alternatively about 0.20 mg to about 1 mg; of the compound of the invention in an aqueous delivery system. The aqueous delivery system may comprise about 0.02% to about 0.5% (w/v) of an acetate, phosphate, or citrate buffer. In another aspect, the formulation has a pH of about 3.0 to about 7.0. In a related aspect, the concentration of the compound in the intravenous formulation falls in the range of about 0.15 μmol/mL to about 0.25 μmol/mL.

In some embodiments, the subject is administered an amount of the compound of the invention in the range of about 3 μg/kg patient (or about 200 μg per patient) to about 60 μg/kg patient (or about 4 mg per patient). The dosage may be administered intravenously as a single bolus injection to the subject, or as single bolus injection followed by a constant infusion for up to 24, 36, 48, or 72 hours, or as a constant infusion for up to 24, 36, 48, or 72 hours. The dosage may be administered subcutaneously or intravenously at intervals not less than 4 hours and for up to 24, 36, 48, or 72 hours. In some embodiments, the subject is administered intravenously for 15 minutes at about 40 μg/min and then about 45 minutes at about 13 μg/min.

In some embodiments, the intravenous formulation is reconstituted from a freeze-dried drug product comprising the compound of the invention. In another embodiment, the freeze-dried drug product further comprises carbohydrate and/or polyhydric alcohols. The carbohydrate may be mannose, ribose, trehalose, maltose, inositol, lactose, or the like. The polyhydric alcohols may be sorbitol, mannitol, or the like. The pharmaceutical composition comprising the Active Agent can also be administered using a nebulizer (i.e., inhaled) or administered enterally, such as orally.

In one embodiment, the liquid formulation comprises the Active Agent in an amount of about 3 μg/mL to about 60 μg/mL, about 6 μg/mL to about 30 μg/mL, and about 12 μg/mL to about 30 μg/mL, and about 15 μg/mL to about 20 μg/mL. In another embodiment, the liquid formulation further comprises dextrose.

EXAMPLES

The following examples are provided to illustrate certain aspects of the present invention and to aid those of skill in the art in practicing the invention. These examples are not intended to limit the scope of the invention. In particular, while the administration of MN-221 is exemplified below, it is anticipated that similar results are obtained using any one of the other members comprising "Active Agent."

Example 1

Safety and Efficacy of In Vivo Administration of MN-221

In preclinical studies, intravenously administered MN-221 (0.04 to 0.4 mg/kg) at the peak of ragweed-induced bronchoconstriction demonstrated a statistically significant, and near maximal reversal of bronchoconstriction in ragweed sensitized dogs between 0.75 and 6.7 min ($p<0.001$ up to 4.5 min and $p<0.01$ up to 6.7 min) after dosing.

In a separate study with telemetered dogs at the Lovelace Respiratory Research Institute, the effect of i.v. MN-221 administration in addition to nebulized albuterol was performed to assess cardiovascular changes and safety of the combination therapy. Albuterol was administered by inhalation at 5 or 10 ug/kg and MN-221 was intravenously administered over 15 min at 0.3, 3, or 30 ug/kg. As expected with beta-agonists and as shown in other model systems, both albuterol and MN-221, alone, increased heart rate to a modest level depending on dose. No adverse changes in MAP or QTc were observed with either agent at any dose. Most importantly and most pertinent to the discovery described herein, when clinically-relevant doses of MN-221 were added on top of clinically-relevant albuterol doses, there was no additional increase in heart rate. See, FIG. 4. And other cardiovascular parameters (MAP, QTc) were not adversely changed with combination therapy.

Example 2

Administration of MN-221 for the Treatment of AEA

MN-221 was tested at escalating doses of 240 μg to 1,080 μg in patients with AEA treated in emergency departments (EDs). The study included 29 (13 treated with SOC only and 16 treated with MN-221 in combination with SOC) patients with severe AEA. All patients were administered SOC treatment as follows: supplemental oxygen given to maintain oxygen saturation measured by pulse oximetry of $\geq 90\%$; two doses of inhaled beta2-agonist (in this study, albuterol 5 mg) via nebulizer given approximately every 20 minutes; simultaneously with two doses of an inhaled anti-cholinergic agent (in this study, ipratropium 0.5 mg) via nebulizer given approximately every 20 minutes; one dose of corticosteroid given orally (in this study, prednisone 60 mg) or intravenously (in this study, methylprednisolone 125 mg), and intravenous magnesium sulfate (2 gm, diluted with 50-100 mL normal saline) and given over 10 minutes to patients with an $FEV_1 \leq 25\%$ of predicted upon ED presentation treatment.

MN-221 was administered at the following doses: 16 μg/min for 15 minutes (total of 240 μg); 30 μg/min for 15 minutes (total of 450 μg); 16 μg/min for 15 minutes; 8 μg/min for 105 minutes (total of 1,080 μg). A lyophilized unit dose for of MN-221, containing 2 mg MN-221 and lactose in a 10 mL vial was employed in the administration. Vials containing 2 mg (2000 μg) of MN-221 and vials containing placebo were reconstituted as follows. 4 mL of 5% dextrose in water was added to each 10 mL vial containing MN-221 to make 500 μg/mL stock solution (2000 μg/4 mL=500 μg/mL). 2 mL (1,000 μg) of stock solution was added to 123 mL 5% dextrose in water to make the total volume of 125 mL (123 mL+2 mL=125 mL). Final MN-221 solution equal to 1,000 μg/125 mL or 8 μg/mL was prepared this way.

Patients were administered SOC treatment (inhaled albuterol, 2.5 mg via nebulizer up to every 20 minutes) and ipratropium (0.5 mg via nebulizer up to every 20 minutes) in addition to treatment with MN-221 or placebo.

The hospital admission rate was lower in the all MN-221 group (4/16 patients, 25%) compared with the placebo group (7/13 patients, 54%). The results demonstrated more than 50% reduction in hospitalization rate among patients treated with MN-221. Improvement in forced expiratory volume in 1 second ($FEV_1$) values generally appeared to be greater for patients receiving MN-221 in addition to SOC treatment. No safety concerns with adding MN-221 to standardized care were identified following review of electrocardiogram (ECG), laboratory, and adverse experience data. This example demonstrates the usefulness of administering MN-221 in accordance with the various aspects and embodiments of the present invention in the treatment of AEA and status asthmaticus.

Example 3

Demonstration of Safety and Efficacy of MN-221 Administration to AEA Patients

A randomized, double-blind, placebo-controlled Phase II clinical trial is performed for demonstrating the efficacy and safety of administering MN-221 in accordance with the various aspects and embodiments of the methods of the present invention. A patient is administered the following initial SOC treatment regimen (consistent with the National Asthma Education and Prevention Program and the Global Initiative for Asthma (GINA) guidelines). The SOC includes the following: supplemental oxygen given to maintain oxygen saturation as measured by pulse oximetry of $\geq 90\%$ as needed; albuterol: 10 mg of albuterol via nebulizer prior to the qualifying spirometry evaluation; simultaneously with ipratropium: 1.0 mg of ipratropium via nebulizer prior to the qualifying spirometry evaluation (if a nebulizer is not used, albuterol and ipratropium may be administered using an MDI with spacer as follows; albuterol: 16 puffs of albuterol (90 μg/puff) via MDI with spacer prior to the qualifying spirometry evaluation, simultaneously with ipratropium: 16 puffs of ipratropium (18 μg/puff) via MDI with spacer prior to the qualifying spirometry evaluation); the patient is assessed for response to that treatment; one dose of at least 50 mg of a corticosteroid given either orally (prednisone) or intravenously (methylprednisolone) or the equivalent dose of another corticosteroid; and treatment with magnesium sulfate, e.g., patients with an $FEV_1 \leq 25\%$ of predicted, benefited from receiving 2 gm of intravenous magnesium sulfate therapy.

In a particular study patients receive during a screening period the following standard treatment (in addition to the albuterol and ipratropium doses received during a pre-screening period): supplemental oxygen given to maintain oxygen saturation as measured by pulse oximetry of $\geq 90\%$ as needed; albuterol: a dose of at least 2.5 mg but not more than 7.5 mg of albuterol via nebulizer to be given during the screening period, simultaneously with ipratropium: a dose of 0.5 mg of ipratropium via nebulizer to be given during the screening period. If a nebulizer is not used, albuterol: a dose of at least 6 puffs but not more than 18 puffs (90 μg/puff) via MDI with spacer to be given during the screening period, simultaneously with ipratropium: a dose of 8 puffs (18 μg/puff) via MDI with spacer to be given during the screening period. If the patient's $FEV_1$ is less than or equal to 50 percent of predicted and the patient meets all other study entry criteria, the patient is randomized to receive either MN-221 or placebo. Patients enrolled in the study receive an intravenous 1-hour infusion of MN-221 study drug or placebo. Two (2) mg Lyophilized unit dose forms of MN-221 are used as dug product. After reconstituting with D5W, an aqueous formulation of 13.3 μg/mL MN-221 is administered to the patients. Patients administered MN-221, receive a total dose of 1200 μg (40 μg/min for 15 min [600 μg]+13.3 μg/min for 45 min [600 μg]); i.e., patients receive 1200 μg over a period of 1 h.

Patients enrolled in the study are administered SOC, as needed, in combination with MN-221 while being administered an intravenous infusion of MN-221, or with placebo. The following SOC is administered. Supplemental oxygen is optionally administered to maintain oxygen saturation as measured by pulse oximetry of $\geq 90\%$ as needed; albuterol: a dose of at least (2.5 mg) but not more than 7.5 mg of albuterol via nebulizer to be administered hourly during the treatment period; ipratropium: a dose of (0.5 mg) of ipratropium via nebulizer is optionally administered hourly during the treatment period. If nebulizers are not used, SOC may be administered by MDI. The primary efficacy endpoint is improvement in $FEV_1$.

Example 4

MN-221 Formulation for Intravenous Administration

MN-221 (2 mg) is formulated as an aseptically processed lyophilized product for injection, as tabulated below.

TABLE 3

| Ingredient | Function | Amount in mg/vial |
| --- | --- | --- |
| MN-221 drug substance | Active ingredient | 2 |
| Polyhydric Alcohol, USP/EP | Filler | 200 |
| Water for Injection, USP/EP | Solvent for production | Removed during lyophilization |
| Nitrogen, NF | To fill vial headspace | QS |

The formulation is administered intravenously after reconstitution with 5 mL of Dextrose Injection 5% or other parenterally acceptable solution.

Example 5

Administration of MN-221 as a First Line Combination Therapy

Patients showing symptoms of exacerbation of asthma, in an emergency department (ED) or in a prehospital setting, are treated by administration of MN-221, as described in Example 5, and additionally an SOC is administered or applied in combination. As part of the SOC, albuterol (about 10 mg) is administered, without or with ipratropium (about 1 mg), via nebulizers. If a nebulizer is not used, albuterol and ipatroprium are administered using an MDI with spacer as follows. For albuterol, about 16 puffs of albuterol (90 μg/puff; and for ipratropium, about 16 puffs of ipratropium (18 μg/puff) are administered. Additionally, some patients are also administered a dose of about 50 mg of a corticosteroid given either orally (prednisone) or intravenously (methylprednisolone). Additionally, some patients are also administered about 2 gm of intravenous magnesium sulfate. Supplemental oxygen is also given to maintain oxygen saturation as measured by pulse oximetry of $\geq 90\%$.

While certain aspects and embodiments of the present technology have been illustrated and described, it will be understood that changes and modifications can be made therein in accordance with ordinary skill in the art without departing from the present technology in its broader aspects as defined in the following claims.

What is claimed:

1. A method of improving one or more clinical outcomes of an individual experiencing an acute exacerbation of asthma, comprising administering to an individual suffering from an acute exacerbation of asthma an effective amount of bedoradrine or a pharmaceutically acceptable salt thereof in combination with a standard of care (SOC) treatment regimen.

2. The method of claim 1 in which the bedoradrine or a pharmaceutically acceptable salt thereof is administered after administration of the SOC treatment regimen.

3. The method of claim 1 in which the bedoradrine or a pharmaceutically acceptable salt thereof is administered contemporaneously with the SOC treatment regimen.

4. The method of claim 1 in which the bedoradrine or a pharmaceutically acceptable salt thereof is administered before administration of the SOC treatment regimen.

5. The method of claim 1 in which the SOC treatment regimen comprises administration of one or more β-agonist bronchodilators, one or more anti-cholinergic drugs, one or more corticosteroids, or combinations thereof.

6. The method of claim 1 in which the SOC treatment regimen includes the administration of magnesium.

7. The method of claim 5 in which the one or more β-agonist bronchodilators, or one or more anti-cholinergic drugs are administered by inhalation, injection, or intravenous infusion.

8. The method of claim 5 in which the one or more β-agonist bronchodilators are selected from albuterol, bitolterol, levalbuterol, pirbuterol, epinephrine, terbutaline, formoterol and salmeterol.

9. The method of claim 5 in which the one or more anti-cholinergic drugs are selected from ipratropium and tiotropium.

10. The method of claim 5 in which the one or more corticosteroids are selected from prednisone, methylprednisolone and prednisolone.

11. The method of claim 1 in which the bedoradrine or a pharmaceutically acceptable salt thereof is administered intravenously.

12. The method of claim 1 in which the bedoradrine or a pharmaceutically acceptable salt thereof is administered orally.

13. The method of claim 1 in which the bedoradrine or a pharmaceutically acceptable salt thereof is administered by inhalation.

14. The method of claim 1 in which the amount of bedoradrine or a pharmaceutically acceptable salt thereof administered to the individual falls in the range of 100 to 5,000 µg.

15. The method of claim 14 in which about 500 to about 1,500 µg of bedoradrine or a pharmaceutically acceptable salt thereof is administered intravenously over a period of about 5 to about 120 minutes.

16. The method of claim 1 in which the patient has been admitted to an emergency room.

17. The method of claim 1 in which the one or more clinical outcomes improved is selected from an increase in $FEV_1$, a reduction in likelihood of hospitalization, an improvement in dyspnea scores, a reduction in incidence of intubation, a reduction in length of stay in an intensive care unit and an improvement in self-ambulation unaccompanied by respiratory distress.

18. The method of claim 17 in which $FEV_1$ improves by 5% or more, 10% or more, or 15% or more.

19. The method of claim 17 in which the likelihood of hospitalization of the individual receiving the combination treatment is reduced compared with an individual receiving only the SOC treatment regimen.

20. The method of claim 19 in which the likelihood of hospitalization of the individual receiving the combination treatment is reduced to about 25% or less, about 20% or less, or about 15% or less.

21. The method of claim 1 in which the individual is not responsive to an inhaled β-agonist bronchodilator.

22. The method of claim 21 in which the inhaled β-agonist bronchodilator is albuterol.

23. The method of claim 1 in which the individual experiences improvement from the acute exacerbation of asthma for about 1 hour or more, about 2 hours or more, about 3 hours or more, about 4 hours or more, about 5 hours or more, about 6 hours or more, or about 8 hours or more after the combination treatment.

24. The method of claim 1 in which the individual experiences improvement in $FEV_1$ (L), $FEV_1$ (% predicted), PEFR, arterial blood oxygen saturation, respiratory rate, or combinations thereof after the combination treatment, unaccompanied by one or more clinically observable adverse events.

25. The method of claim 24 in which the one or more clinically observable adverse events is selected from an increased heart rate, an increased blood glucose, tremor, headache, palpitations and a jittery feeling.

26. A method of alleviating one or more negative effects of an acute exacerbation of asthma, comprising administering to a patient, who has been diagnosed as suffering from an acute exacerbation of asthma, an effective amount of bedoradrine or a pharmaceutically acceptable salt thereof.

27. The method of claim 26 in which the bedoradrine is administered intravenously, orally, or by inhalation.

28. The method of claim 27 in which the patient fails to respond to the SOC treatment regimen.

29. The method of claim 27 in which the patient experiences improved $FEV_1$ relative to the patient's pre-treatment $FEV_1$ and the improved $FEV_1$ persists on average for at least about 6 hours at a level that is about 50% or more of a peak effect.

30. The method of claim 27 in which the daily amount of bedoradrine or a pharmaceutically acceptable salt thereof administered to the patient falls in the range of about 300 to 1500 µg.

* * * * *